United States Patent [19]

Bhatty

[11] Patent Number: 5,518,710
[45] Date of Patent: May 21, 1996

[54] METHODS FOR EXTRACTING CEREAL β-GLUCANS

[75] Inventor: Rattan S. Bhatty, Saskatoon, Canada

[73] Assignee: University of Saskatchewan, Saskatoon, Canada

[21] Appl. No.: 180,088

[22] Filed: Jan. 11, 1994

[51] Int. Cl.$^6$ .............. A61K 35/78; C07H 1/00; C07H 1/06; C08B 37/00
[52] U.S. Cl. .............. 424/195.1; 536/123.1; 536/123.12; 536/124; 536/127; 536/128; 127/34; 127/36; 127/38; 127/39; 127/40
[58] Field of Search .............. 424/195.1; 536/123.1, 536/123.12, 124, 127, 128; 127/34, 36, 38, 39, 40; 435/200, 201; 426/18, 28

[56] References Cited

U.S. PATENT DOCUMENTS

| | | | |
|---|---|---|---|
| 4,233,406 | 11/1980 | Wieg et al. | 435/275 |
| 4,247,636 | 1/1981 | Schoenrock et al. | 435/94 |
| 4,366,173 | 12/1982 | Parker | 426/20 |
| 4,428,967 | 1/1984 | Goering et al. | 426/28 |
| 4,804,545 | 2/1989 | Goering et al. | 426/28 |
| 4,957,565 | 9/1990 | Lehmussaari et al. | 127/68 |
| 4,960,705 | 10/1990 | Johann et al. | 435/272 |
| 5,013,561 | 5/1991 | Goering et al. | 426/28 |
| 5,082,673 | 1/1992 | Inglett | 426/21 |
| 5,151,283 | 9/1992 | Foehse et al. | 426/93 |
| 5,169,660 | 12/1992 | Collins et al. | 426/271 |
| 5,190,755 | 3/1993 | Molin et al. | 424/93 J |
| 5,200,215 | 4/1993 | Slade et al. | 426/18 |
| 5,362,502 | 11/1994 | Slade et al. | 426/20 |
| 5,380,542 | 1/1995 | Jenkins et al. | 426/573 |

OTHER PUBLICATIONS

Palmer et al. *J. Inst. Brew*, vol. 92(5), pp. 461–462, (1986).
Dawkins et al. *Journal of Food Science*, vol. 58(3), pp. 562–566, (1993).
Ahluwalia et al., *J. Inst. Brew*, vol. 90(4), pp. 254–259, (1984).
Ullrich et al. *Journal of Cereal Science*, vol. 4(3), pp. 279–285, (1986).
Gruppen et al. *J. Cereal Sci.*, vol. 13(3), pp. 275–290, (1991).
Knuckles et al. *Cereal Chemistry*, vol. 69(2), pp. 198–202, (1992).
R. S. Bhatty "Extraction and Enrichment of (1→3),(1→4)–β–D–Glucan from Barley and Oat Brans" *Cereal Chem.* (Jan. 12, 1994) 70:73–77.

*Primary Examiner*—Douglas W. Robinson
*Assistant Examiner*—Howard C. Lee
*Attorney, Agent, or Firm*—Reed & Robins

[57] ABSTRACT

Simple and efficient methods for extracting high levels of β-glucans from cereal sources are disclosed. The method employs a strong base, such as sodium hydroxide as an initial solvent. If desired, the extract can be further purified to render a β-glucan preparation which can be used directly or stored for future use.

8 Claims, 2 Drawing Sheets

Barley bran + 0.25 N NaOH; Repeat extraction one more time if necessary.

Centrifuge, combine supernatants where necessary. Adjust pH to 6.5 with HCL Add calcium chloride(70 mg/L), then Termamyl (0.1 ml/100 ml of supernatant) and incubate at 80 C for 1 hour with shaking.

Cool to room temperature, add sufficient HCl to pH 4.5, centrifuge and discard pellet.

Add ethanol to 50% concentration, let stand to precipitate B-Glucan.

Centrifuge, discard supernatant. Wash pellet 2 times with 50% ethanol, centrifuge, suspend the final pellet in water, lightly homogenize and freeze-dry.

FIG. 2

METHODS FOR EXTRACTING CEREAL β-GLUCANS

BACKGROUND OF THE INVENTION

1. Technical Field

The present invention relates generally to glucans. More particularly, the invention relates to methods for extracting β-glucans from cereal sources.

2. Background of the Invention

Glucans are structural polysaccharides present in the cell wall of yeasts, fungi and cereals. For example, (1→3)-,(1→4)- and mixed (1→3), (1→4)-β-D-glucans are found in the endosperm cell wall of such cereals as barley and oat, among others. β-Glucans affect the viscosity and hence the effectiveness of products derived from these sources. For example, the presence of β-glucans in animal feed products is often undesirable. On the positive side, β-glucans appear to influence digestion, assist in glucoregulation and lower serum cholesterol. Cereal β-glucans are useful nutritional agents and have also been used as bulking agents in place of sucrose. Accordingly, efficient methods for removing unwanted β-glucans from cereal sources, as well as purifying them for future use and study, are needed.

β-Glucans have been extracted from oat flour and bran using a sodium carbonate solution and purified for analytical and nutritional purposes. Wood et al. *Cereal Chem.* (1978) 55:1038–1049; Welch et al. *Nutr. Rep. Int.* (1988) 38:551–561; Wood et al. *Cereal Chem.* (1989) 66:97–103. Wood et al. *Cereal Chem.* (1991) 68:31–39; and Wood et al. *Cereal Chem.* (1991) 68:530–536, describe the molecular characterization of oat β-glucans. Knuckles et al. *Cereal Chem.* (1992) 69:198–202, describe the extraction of β-glucan from barley and oats using dry milling and sieving. Such techniques offer advantages over wet extraction where solvent disposal may be a problem. However, dry milling and sieving techniques result in the presence of considerable starch and other components which may interfere with certain β-glucan applications.

DISCLOSURE OF THE INVENTION

The present invention provides for a simple and efficient method of extracting high levels of β-glucans from cereal brans.

Accordingly, in one embodiment the invention is directed to a method for extracting a β-glucan from a cereal source comprising mixing a β-glucan-containing cereal with a basic solution under conditions sufficient to extract the β-glucan from the cereal, thereby producing a β-glucan extract.

In another embodiment, the invention is directed to a method for extracting a β-glucan from barley bran comprising mixing the barley bran with a sodium hydroxide solution under conditions sufficient to extract the β-glucan from the barley bran, thereby producing a β-glucan extract.

In yet another embodiment, the invention is directed to a method for extracting a β-glucan from oat bran comprising mixing the oat bran with a sodium hydroxide solution under conditions sufficient to extract the β-glucan from the oat bran, thereby producing a β-glucan extract.

In further embodiments, the invention is directed to a method of purifying the β-glucan extract by the steps comprising:

(a) adding an amylolytic agent to the extract under conditions which allow for the degradation of contaminating starches;

(b) removing degraded starches from the extract of step (a); and (c) adding a polar alcohol to the product of step (b) to precipitate β-glucan therefrom.

These and other embodiments of the subject invention will readily occur to those of ordinary skill in the art in view of the disclosure herein.

BRIEF DESCRIPTION OF THE FIGURES

FIG. 2 is a flow diagram depicting the β-glucan purification procedure described in Example 3.

DETAILED DESCRIPTION OF THE INVENTION

Figure 1:
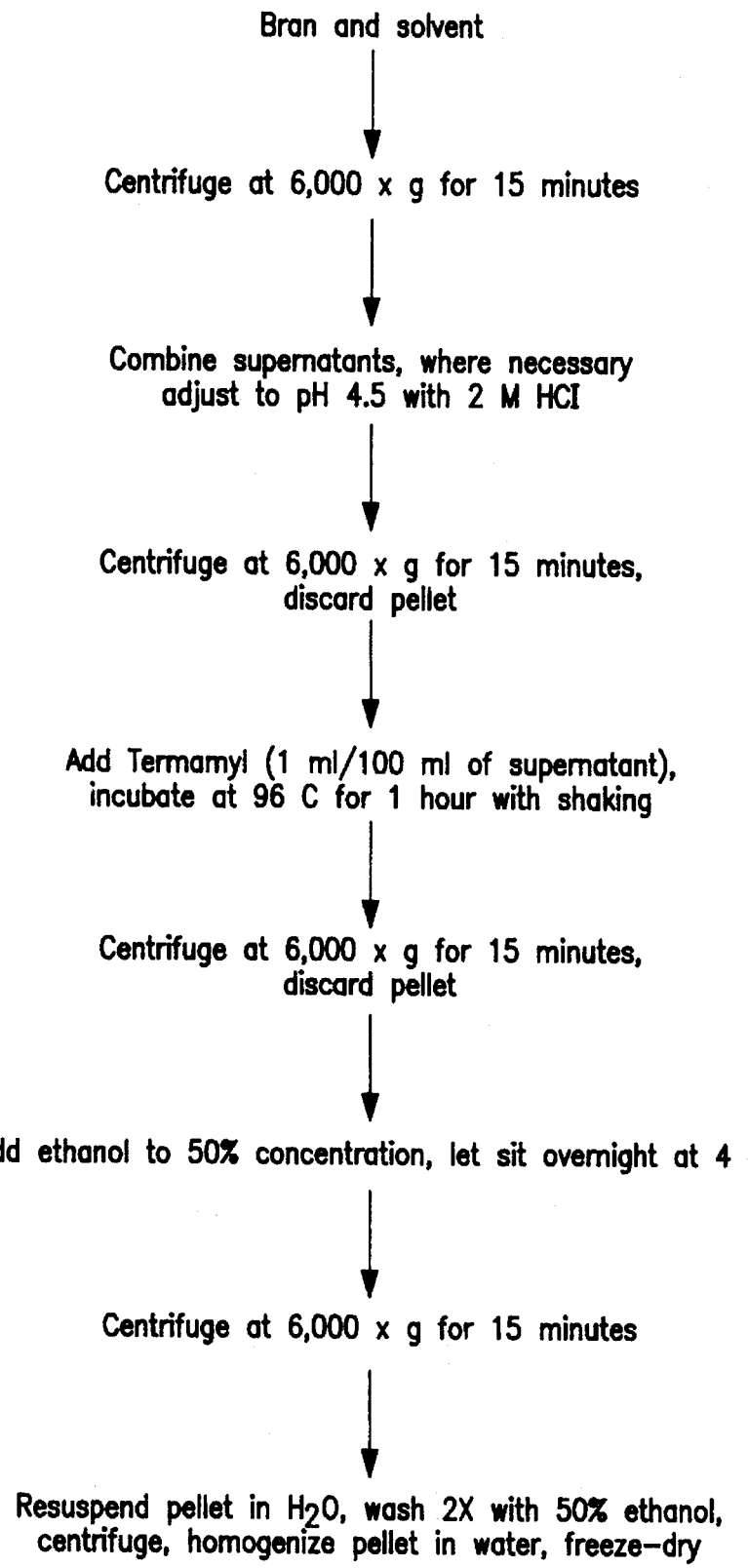
FIG. 1 is a flow diagram depicting the β-glucan purification procedure described in Examples 1 and 2.

The practice of the present invention will employ, unless otherwise indicated, conventional methods of chemistry, cereal chemistry and biochemistry, within the skill of the art. Such techniques are explained fully in the literature. See, e.g., *Barley: Chemistry and Technology*, MacGregor, A. W. and Bhatty, R. S. eds. (American Association of Cereal Chemists, Inc., St. Paul, Minn.).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, the term "a β-glucan" can include more than one β-glucan.

A. Definitions

In describing the present invention, the following terms will be employed, and are intended to be defined as indicated below.

By "cereal" is meant any of several cereal grains such as, but not limited to, any of the various cultivars of barley, oat, wheat, rye, corn, sorghum and millet.

By "β-glucan" is meant a glucan with a β(1→3)-linked glucopyranose backbone, or a β(1→4)-linked glucopyranose backbone or a mixed β(1→3),(1→4)-linked glucopyranose backbone.

A "β-glucan extract" is a preparation which includes a β-glucan and which has been produced by the treatment of a β-glucan-containing source using the methods described herein.

A "cereal β-glucan" or a "cereal β-glucan extract" is a β-glucan or a β-glucan extract, respectively, which is derived from a cereal source.

B. General Methods

Central to the present invention is the discovery of a simple and efficient method for extracting high levels of β-glucans from cereal sources. The method employs a strong base as an initial solvent, which as shown herein, provides for increased extraction of β-glucans than the prior art methods. The extract can be further purified to render a β-glucan preparation which can be used directly or stored for future use and which provides a source of soluble dietary fiber for analytical, therapeutic and nutritional purposes.

Using the methods of the present invention, it is possible to extract at least about 20% or more of the β-glucans present in the cereal source, more usually at least about 40% or more of the β-glucans, and preferably at least about 50% to about 70% or more, of the β-glucans from the cereal source. Thus, the methods described herein serve at least two purposes. First, unwanted β-glucans can be eliminated from the cereal source, e.g., in the case of animal feeds where the presence of β-glucans is often undesirable. The extracted β-glucans can be discarded, or conversely, further purified for future use. Thus, the methods described herein also provide for the preparation of relatively pure extracts for analytical and dietary uses.

Any of several known cereals can be used in the process of the present invention. Such cereals include, without limitation, any of the various cultivars of e.g., barley, oat, wheat, rye, corn, sorghum and millet, with barley and oat preferred due to their high β-glucan levels.

Cereal flours, brans and even commercially available breakfast cereals derived from the grains described above, can be used as sources of β-glucans in the process of the present invention. Cereal flours and brans are commercially available from a number of sources or can be produced from the cereal in question using standard milling techniques such as described in e.g., Bhatty, R. S. *Cereal Chem.* (1986) 63:31–35; Wood et al. *Cereal Chem.* (1989) 66:97–103; Wood et al. *Cereal Chem.* (1991) 68:31–39, and well known to those of skill in the art.

The cereal product is then mixed with a basic solution under conditions sufficient to extract the β-glucans present in the cereal source. For most cereals, a basic solution having a pH from about 8 to about 14, more preferably, from about 8 to about 12, and most preferably from about 10 to about 12, will be adequate for extracting the β-glucans. The pH of the base will depend on the conditions used during the extraction. For example, a higher pH can be used if a shorter extraction time is desired. Furthermore, if the β-glucan extract will be further purified, rather than discarded, the pH of the base will be such that the β-glucan molecule remains generally intact.

The base used will generally be an inorganic base such as, but not limited to, NaOH, KOH, $NaHCO_3$ and $Na_2CO_3$. The extraction time will vary, depending on the cereal and base used, as well as the concentration of the base and the treatment temperature. It has been found that the addition of 0.25N NaOH at a ratio of about 1:10 to about 1:100 of cereal to solvent, more generally, about 1:20 to about 1:60 of cereal to solvent, incubated for from about 2 to about 25 hours, more usually about 4 to about 20 hours, at about 15° to about 35° C., will provide adequate conditions for the extraction of β-glucans. The base-treatment can be repeated under similar or variable conditions, if so desired.

The base-soluble β-glucans can then be separated from the solution using an appropriate separation technique such as centrifugation, dialysis or filtration. The pH of the resulting supernatant is then adjusted to about pH 2 to about pH 9, more preferably about pH 3 to about pH 8 and most preferably about pH 4 to about pH 7, using an acid solution such as HCl.

Following acid treatment the solution can be centrifuged and an amylolytic agent, for example an α-amylase preparation such as Termamyl, added to eliminate, in whole or part, contaminating starches. Generally, the solution will then be allowed to incubate with shaking for approximately 30 to 120 minutes, more about preferably 60 to 100 minutes, at about 40° to about 100° C., more preferably about 80° to about 100° C. Prior to treatment with the amylolytic agent, a salt, such as, but not limited to $CaCl_2$, $CaOH_2$, $CaCO_3$ and CaO, can be added to enhance the action of the amylolytic agent. Following treatment with the amylolytic agent, the degraded starches are removed using a suitable separation technique such as centrifugation, dialysis or filtration, and a polar alcohol, for example an alkyl alcohol such as methanol, ethanol, propanol, butanol etc., can be added to precipitate β-glucan. Generally, the alcohol will be added to a final concentration of about 20% to about 90%, more preferably about 30% to about 70%, and more usually from about 40% to about 60% and the solution allowed to stand until a precipitate forms. The solution is then centrifuged, the pellet resuspended and washed and the resulting pellet homogenized. The solution can be used directly or stored for the future.

The β-glucan content of the final extract can be determined using a number of methods, known to those of skill in the art. For example, β-glucan content can be assessed colorimetrically and/or by standard analytical techniques such as size exclusion chromatography (SEC) and HPLC. See, e.g., Wood et al. *Cereal Chem.* (1977) 54:524; Wood et al. *Cereal Chem.* (1991) 68:31–39; and Wood et al. *Cereal Chem.* (1991) 68:530–536. β-Glucans can also be analyzed enzymatically using commercially available kits, such as the Biocon K-133 kit (Biocon U.S.A., Lexington, Ky.), employing the techniques of McCleary and Glennie-Holmes *J. Inst. Brew.* (1985) 91:285 or by viscometric measurements such as described by Manners and Marshall *J. Inst. Brew.* (1969) 75:550 and Wood et al. *Cereal Chem.* (1978) 55:1038–1049, using substrates such as oat gum, carboxymethyl-pachyman (Clarke and Stone *Phytochemistry* (1962) 1:175), and hydroxyethylcellulose.

Using the above-described methods, it is possible to extract as much as 50% to 80% or more of the β-glucans present in the initial cereal product.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials

Tupper (six-rowed) registered Canadian hull-less barley containing low β-glucan (4.5%) was grown at the University of Saskatchewan, Saskatoon, North Seed Farm. Azhul (high β-glucan, 11.3%), a six-rowed waxy hull-less barley, was a gift from W. Newman of Montana State University, Bozeman. Oat bran was a commercial product obtained from RobinHood Multifoods, Saskatoon. Tupper and Azhul barleys were dry-milled to obtain bran in about 30% yields, using a short-flow milling procedure in an Allis-Chalmers experimental mill (Allis-Chalmers, Milwaukee, Wis.) (Bhatty, R. S., *Cereal Chem.* (1986) 63:31– 35). The barleys and oat bran were ground in a Udy cyclone mill (Udy, Fort Collins, Colo.) to pass through a 1.0 mm screen.

The assay kit for β-glucan determination and commercial β-glucan (about 77% purity) were obtained from Biocon US Ltd. (Lexington, Ky.). Termamyl 120 L (α-amylase) was from Novo Industrie A/S Copenhagen, Denmark. TSK-Gel (Toyopearl), HW-65, particle size 30 to 60 μm, fractionation range $10^4$ to $10^7$ Da, was purchased from Supelco, Bellefonte, Pa.

Extraction and Purification of β-glucan

Tupper barley bran and oat bran were extracted with solvent 1 only. Azhul barley bran was extracted with solvent 1 and with two more solvents. Solvent 1 was distilled water adjusted to pH 10 with 20% sodium carbonate. The ratio of bran to solvent was 1:10, and extraction time was 30 minutes at 45° C. (Wood et al. *Cereal Chem.* (1989) 66:97–103). Solvent 2 was distilled water adjusted to pH 7, and the ratio of bran to solvent was 1:10. The extraction was performed sequentially at 40°, 65° and 95° C., and then the three supernatant fractions were combined (McCleary, B. V., in *Alternative End Uses of Barley* (1988) D. H. B. Sparrow et al. eds., page 117, Waite Agricultural Research Institute: Glen Osmond, Australia). Solvent 3 was 4% (0.25N) sodium hydroxide solution. The ratio of bran to solvent was 1:50, and extraction time was 18 hours at room temperature (Carr et al., *Cereal Chem.* (1990) 67:226–229). The rest of the procedure used for purification of the extracts in Examples 1 and 2 was identical in each case (see FIG. 1). The procedure used for purification of the extract in Example 3 is shown in FIG. 2.

Analysis

Total β-glucan (brans and the freeze-dried preparations), extractable β-glucan (extracts), and nonextractable β-glucan (residues) were determined by the procedure of McCleary and Glennie-Holmes *J. Inst. Brew.* (1985) 91:285–295. Acid extract viscosity, pentosans ([arabinose+xylose]×0.88), and monosaccharides (by gas-liquid chromatography) were determined as described by Bhatty et al. *Cereal Chem.* (1991) 68:221–227. Starch analysis was performed by the procedure of Fleming and Reichert *Cereal Chem.* (1980) 57:153–154; total nitrogen, ether extract, and ash were determined by using AOAC Official Methods Official Methods of Analysis, 15th ed. (1990) The Association of Official Analytical Chemists, Arlington, Va. For column chromatography, the TSK-Gel was prepared in 100 mM sodium acetate buffer, pH 5.4, according to the manufacturer's instructions and packed into a glass column (100×1.6 cm; total volume about 208 ml). Void volume (75 ml) and elution volume (127 ml) were determined with blue dextran (Sigma; average molecular weight $2 \times 10^6$). About equal concentrations of the purified β-glucan and commercial β-glucan were dissolved in the acetate buffer by heating (<70° C.) and were eluted from the column with the buffer at a flow rate of about 15 ml/min. Lichenase (0.2 ml) was added to 1.0-ml aliquots of the fractions, and the assay mixture was incubated for 1 hour at 40° C. To a 100-µl aliquot of the mixture, 0.2 ml of β-glucosidase was added and incubated at 40° C. for 20 minutes. The glucose released was measured at 510 mm, using glucose oxidase-peroxidase reagent (McCleary and Glennie-Holmes, *J. Inst. Brew.* (1985) 91:285–295).

Example 1

Extraction of β-glucan using Solvent 1

In a preliminary experiment, tupper barley bran (6.6% β-glucan) and commercial oat bran (6.9% β-glucan) were extracted in 5-g quantities with solvent 1, and proportions of the extractable and nonextractable β-glucans were calculated as percentage of the total β-glucan. In barley bran, about 70% of the β-glucan was extracted, whereas in oat bran the extractability was 81% (Table I). The rest was nonextractable β-glucan. Extractability of β-glucan from oat bran, on the basis of triplicate determination, had variability similar to extractability of barley bran β-glucan. In both cases, the coefficient of variation was about 8%. Although at this stage solvents were not compared for extractability of barley or oat bran β-glucan, as shown in Example 2, it was found (Table II, solvent 3) that sodium hydroxide considerably improved the extractability of β-glucan from barley bran.

TABLE I

Repeatability of β-glucan Extraction from Barley and Oat Brans[a]

| | Barley Bran (6.6% β-glucan) | | Oat Bran (6.9% β-glucan) | |
|---|---|---|---|---|
| | Extractable[b] | Non-extractable[c] | Extractable | Non-extractable |
| | 67.6 | 32.4 | 75.1 | 24.9 |
| | 70.5 | 29.5 | 87.7 | 12.3 |
| | 62.2 | 37.8 | 78.0 | 22.0 |
| | 71.0 | 29.0 | | |
| | 76.9 | 23.1 | | |
| Mean | 69.6 | 30.4 | 80.3 | 19.7 |
| Standard deviation | 5.4 | 5.4 | 6.6 | 6.6 |
| Coefficient of variance | 7.8 | 17.8 | 8.2 | 33.5 |

[a]Shown as percentage of tat β-glucan
[b]Solvent 1 (20% sodium carbonate, pH 10), see Materials and Methods for details.
[c]Determined on oven-dried residue; extractable and nonextractable β-glucan are adjusted to toal 100%

Example 2

Comparison of Solvents 1, 2 and 3 for the Extraction of β-glucan

Barley and oat brans were extracted in 5- or 40-g quantities to determine mass balance of β-glucan and its recovery from the extractable fraction by following the purification procedure outlined in FIG. 1. In barley brans, the extractable β-glucan was 61 and 63% for solvent 1, 72% for solvent 2, and 84% for solvent 3 (Table II). With oat bran, solvent 1 extracted 70% of the β-glucan, which was lower than the average obtained for the same solvent in Table I (80%). Extractability of β-glucan is critical, as it will determine the final yield of the preparation. Sodium hydroxide (solvent 3) extracted more β-glucan from Azhul barley bran (84%) compared with extraction from the same bran with solvent 1 (61%) or solvent 2 (72%). The residue, in each case vacuum-dried overnight at 60° C., was used to determine nonextractable β-glucan. The two fractions (extractable and nonextractable) accounted for 96–98% of the total β-glucan for solvent 1, 95% for solvent 2, 100% for solvent 3 and 90% for solvent 1 in oats. Table II also gives the final recoveries (yields) of β-glucan from the extractable fractions. The highest recovery was obtained with solvent 3 for a final β-glucan yield of 81% of that present in Azhul barley bran. With other solvents the recoveries were lower and variable; solvent 2 had the lowest (40%) followed by solvent 1 (52–61%) in barley and oat brans. Thus, yield differences were greater for the extraction solvents in Azhul barley bran than for solvent 1 in different brans.

Table III gives the comparative compositions of the β-glucan preparations. All of the preparations contained less than 1% total nitrogen, 0.4–1.2% starch, 3.7–12.6% ash, and 1.1–10.9% pentosan; ether extract was not detected in any of the preparations. The variable and high ash content of the preparations was most likely sodium chloride, which was easily washed out with 50% ethanol. One β-glucan preparation from Azhul barley bran, extracted with sodium hydroxide (solvent 3,) was dialyzed overnight against distilled water. This reduced the ash content from 12.6 to 3.3% However, washing of the preparations with 50% ethanol before freeze-drying was preferable. The other highly variable component was the pentosans, undoubtedly because of their variability in the brans and also because of differences in solubility in different solvents. The β-glucan preparations from barley brans contained more pentosans than the preparation from oat bran. the solvent effect was even greater. β-Glucan preparations from Azhul barley bran extracted with solvent 3 contained 10.9% pentosans, compared with 1.9% for the same bran extracted with solvent 2 and 2.9% extracted with solvent 1. This was not surprising as sodium hydroxide is a common solvent for extraction of hemicelluloses or pentosans from cereals. The differences in ash and pentosan contents of the preparations affected their β-glucan concentration or purity. Therefore, for a better comparison of β-glucan and pentosan concentrations, both of which affect viscosity, data were reported as the sum of β-glucan and pentosans expressed on ash-free basis. On this basis, Tupper bran preparations contained 73%, Azhul barley bran preparations 78–82%, and oat bran preparation 84% β-glucan plus pentosans. Thus, extraction of Azhul barley bran with solvents 2 and 3 gave β-glucan preparations with a generally similar purity (81–82%) as that obtained from oat bran extracted with solvent 1 (84%). However, purity of the preparation needs to be evaluated in conjunction with yield or percentage of the total β-glucan recovered. The latter values are reported in Table II. These two expressions were taken to calculate an "enrichment index": yield× (concentration of β-glucan+pentosans, ash-free basis)/100. This expression, given at the bottom row of Table II, showed solvent 3 to be the better solvent for enrichment of β-glucan. Its enrichment index was 65, compared with values of 33 to 43 obtained for the other solvents used for barley brans and 51 for solvent 1 used for oat bran. (Table II).

The major monosaccharide of the preparations was glucose, derived largely from β-glucan and to a minor extent from the contaminating starch (Table III). Azhul barley bran extracted with solvent 1 contained, for unknown reason, less glucose. Arabinose, galactose, and xylose were the other sugars. Fucose and rhamnose were present only in minute quantities. Arabinose and xylose were the next major sugars; the sum of these two in β-glucan preparation obtained with solvent 3 was four to six times higher than in the preparations obtained from the same bran extracted with solvents 1 and 2.

The three β-glucan preparations from Azhul barley bran extracted with solvents 1–3 were fractionated by size-exclusion chromatography to compare their apparent molecular weights with that of the commercial β-glucan. All four preparations eluted largely between the void volume (75 ml) and the elution volume (128 ml) of blue dextran, suggesting apparent average molecular weights approximately in the region of $2\times10^5$. the β-glucan preparations extracted with solvents 2 and 3 eluted in a similar manner, and their molecular weights seemed somewhat larger than that of the commercial β-glucan, which in turn had larger molecular weight than the solvent 1 preparation. Solvent 1 preparation was more heterogenous than the other two preparations. Although equal concentrations of β-glucan for the three preparations were applied to the column, the peak height of solvent 1 preparation was lower and asymmetrical.

Although β-glucan extracted with solvents 2 and 3 seemed to have higher molecular weights than that extracted with solvent 1, the same relationship was not apparent in their acid extract viscosity. The reverse seemed to be the case for the solvent 1 preparations, which had the highest flow viscosity. The preparations of solvents 2 and 3 had similar viscosity.

Thus, of the three solvents compared for β-glucan extraction and purification from barley brans, sodium hydroxide (solvent 3) was most efficient. A single extraction for 17 hours at room temperature at a ratio of meal to solvent of 1:50 extracted 80–85% of the bran β-glucan. Subsequent experiments (not given) showed that the ratio of meal to solvent could be reduced to 1:20 and the extraction time to 6 hours without affecting the extractability of the β-glucan; a second extraction under these conditions removed an additional 4% of the bran β-glucan. The final preparation obtained with this solvent contained generally the same concentration of β-glucan (and pentosans) expressed on ash-free basis (81%) as that obtained from oats with solvent 1 (Table III). The β-glucan yield or percentage of total recovered with this solvent from Azhul barley bran was 81% and its enrichment index 65, which considered yield and purity of the preparations, both being the highest compared with similar values obtained with the other two solvents used for extraction and purification of β-glucan from barley or oat bran (Table II). In addition, sodium hydroxide extracted more pentosans than other solvents. These non-starch polysaccharides enhance the viscometric properties of β-glucan, a desirable feature in food applications.

TABLE II

Mass Balance of β-Glucan
Extracted from Barley and Oat Brans (5 or 40 g) with Different Solvents[a]

| β-Glucan | Tupper Bran | | Azhul Bran | | | | | | Oat Bran | |
| | Solvent 1 | | Solvent 1 | | Solvent 2 | | Solvent 3 | | Solvent 1 | |
| | (mg) | (%) | (mg) | (%) | (mg) | (%) | (mg) | (%) | (mg) | (%) |
|---|---|---|---|---|---|---|---|---|---|---|
| Total | 2,632 | 100 | 5,232 | 100 | 671 | 100 | 671 | 100 | 2,776 | 100 |
| Extractable | 1,670 | 63 | 3,211 | 61 | 486 | 72 | 566 | 84 | 1,932 | 70 |
| Non-Extractable | 914 | 35 | 1,803 | 35 | 152 | 23 | 105 | 16 | 544 | 20 |
| Recovered | 2,584 | 98 | 5,014 | 96 | 638 | 95 | 671 | 100 | 2,476 | 90 |
| Recovered from extractable | 1,367 | 82 | 2,850 | 89 | 265 | 55 | 545 | 96 | 1,692 | 88 |
| Percent total recovered (yield) | | 52 | | 55 | | 40 | | 81 | | 61 |
| Enrichment index[b] | | 38 | | 43 | | 33 | | 65 | | 51 |

[a]Single extraction and purification from each bran with each solvent. Tupper bran, 6.6% β-glucan; Azhul bran, 13.4% β-glucan; oat bran, 6.9% β-glucan.
[b]Defined a yield x (concentration of β-glucan + pentosans on ash-free basis)/100.

TABLE III

Composition of β-Glucan
Preparations isolated from Barley and Oat Brans[a] (%, as is)

| Component | Tupper Bran Solvent 1 | Azhul Bran Solvent 1 | Azhul Bran Solvent 2 | Azhul Bran Solvent 3 | Oat Bran Solvent 1 |
|---|---|---|---|---|---|
| β-Glucan | 57.9 ± 1.0 | 71.9 ± 0.4 | 74.9 ± 2.4 | 59.7 ± 0.3 | 79.7 ± 0.8 |
| Nitrogen | 0.5 ± 0.0 | 0.5 ± 0.0 | 0.6 ± 0.0 | 0.2 ± 0.0 | 0.5 ± 0.0 |
| Starch | 1.1 ± 0.1 | 0.4 ± 0.0 | 1.0 ± 0.1 | 0.4 ± 0.0 | 1.2 ± 0.0 |
| Ether extract | 0 | 0 | 0 | 0 | 0 |
| Ash | 9.5 ± 0.3 | 3.9 ± 0.6 | 6.8 ± 0.2 | 12.6 ± 0.2 | 3.7 ± 0.3 |
| Pentosans | 7.8 ± 0.3 | 2.9 ± 0.0 | 1.9 ± 0.1 | 10.9 ± 0.0 | 1.1 ± 0.0 |
| β-glucan and Pentosans[b] | 65.7 (72.6) | 74.8 (77.8) | 76.8 (82.4) | 70.6 (80.8) | 80.8 (83.9) |
| Monosaccharides | | | | | |
| Arabinose | 3.4 ± 0.2 | 1.2 ± 0.0 | 0.7 ± 0.0 | 4.5 ± 0.1 | 0.5 ± 0.0 |
| Fucose | 0.1 ± 0.0 | 0.1 ± 0.0 | 0.1 ± 0.0 | 0.2 ± 0.1 | 0.1 ± 0.0 |
| Galactose | 1.1 ± 0.1 | 0.4 ± 0.1 | 1.9 ± 0.1 | 2.2 ± 0.1 | 1.2 ± 0.3 |
| Glucose | 49.3 ± 3.5 | 47.9 ± 0.5 | 54.0 ± 0.5 | 62.2 ± 1.2 | 61.3 ± 0.1 |
| Phamnose | 0 | 0 | 0.2 ± 0.0 | 0.1 ± 0.0 | 0 |
| Xylose | 5.4 ± 0.3 | 2.1 ± 0.1 | 1.5 ± 0.0 | 8.0 ± 0.1 | 0.8 ± 0.0 |

[a]Data are means of duplicate determination (means and standard deviations).
[b]Figures in parentheses are on ash-free basis.

Example 3

Extraction of β-glucan from Barley Using Solvent 3

Tupper hull-less barley bran, prepared as described in the Materials and Methods, as well as barley flour, barley meal and ground barley, were treated as in Example 2, with the procedure shown in FIG. 2, as well as with 1.0N NaOH. The procedure resulted in high levels of β-glucan extraction from the barley sources. Results of the extraction from barley flour are shown in Table IV.

TABLE IV

Mass Balance of β-Glucan Extracted from Azhul Barley Flour with 0.1 N NaOH

| | Concentration (mg) | (%) |
|---|---|---|
| β-Glucan | 1,710 | 100 |
| Extractable | 1,443 | 95 |
| Non-Extractable | 78 | 5 |
| Recovered | 1,521 | 100 |
| Recovered from extractable | 1,263 | 88 |
| Percent total recoverd (yield) | | 74 |
| Enrichment index | | 66 |

Thus, novel methods for the extraction and purification of β-glucans from cereal sources have been disclosed. Although preferred embodiments of the subject invention have been described in some detail, it is understood that obvious variations can be made without departing from the spirit and the scope of the invention as defined by the appended claims.

I claim:

1. A method for extracting a β-glucan from bran comprising (a) combining a β-glucan-containing bran with a basic solution having a pH greater than 10, said combining being done for from about 2 to about 25 hours at a temperature of about 15° C. to about 35° C., thereby producing a β-glucan extract, (b) adding an amylolytic agent to said extract to degrade contaminating starches; (c) removing degraded starches from said extract of step (b); and (d) adding a polar alcohol to the product of step (c) to precipitate β-glucan therefrom.

2. The method of claim 1 wherein said cereal is barley bran.

3. The method of claim 1 wherein said cereal is oat bran.

4. The method of claim 1 wherein said basic solution is a sodium hydroxide solution.

5. The method of claim 2 wherein said basic solution is a sodium hydroxide solution.

6. The method of claim 3 wherein said basic solution is a sodium hydroxide solution.

7. A method for extracting a β-glucan from barley bran comprising (a) combining said barley bran with a sodium hydroxide solution wherein said sodium hydroxide solution is about 0.25N to about 1.0N, said combining being done for from about 2 to about 25 hours at a temperature of about 15° C. to about 35° C., thereby producing a β-glucan extract, (b) adding an amylolytic agent to said extract to degrade contaminating starches; (c) removing degraded starches from said extract of step (b); and (d) adding a polar alcohol to the product of step (c) to precipitate β-glucan therefrom.

8. A method for extracting a β-glucan from oat bran comprising combining said oat bran with a sodium hydroxide solution wherein said sodium hydroxide solution is about 0.25N to about 1.0N, said combining being done for from about 2 to about 25 hours at a temperature of about 15° C. to about 35° C., thereby producing a β-glucan extract, (b) adding an amylolytic agent to said extract to degrade contaminating starches; (c) removing degraded starches from said extract of step (b); and (d) adding a polar alcohol to the product of step (c) to precipitate β-glucan therefrom.

* * * * *